United States Patent
Loomis et al.

(10) Patent No.: US 6,797,311 B2
(45) Date of Patent: Sep. 28, 2004

(54) PROCESS FOR IMPREGNATING A POROUS MATERIAL WITH A CROSS-LINKABLE COMPOSITION

(75) Inventors: Gary L. Loomis, Morristown, NJ (US); Bruce Parsons, Pompan Beach, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/359,497

(22) Filed: Feb. 6, 2003

(65) Prior Publication Data

US 2003/0143330 A1 Jul. 31, 2003

Related U.S. Application Data (63) Continuation of application No. 09/433,625, filed on Nov. 3, 1999, now Pat. No. 6,521,284.

(51) Int. Cl.[7] .............................. B05D 1/00; A61L 27/00
(52) U.S. Cl. ...................... 427/2.24; 427/2.1; 427/2.25; 427/2.3; 427/2.31; 427/209; 427/230; 427/238; 427/294; 427/296
(58) Field of Search .............................. 427/2.1, 2.25, 427/2.24, 2.3, 2.31, 209, 230, 238, 294, 296

(56) References Cited

U.S. PATENT DOCUMENTS

| | | | |
|---|---|---|---|
| 3,340,119 A | 9/1967 | Wiltshire et al. | |
| 3,925,576 A | 12/1975 | Hendrix | |
| 3,975,479 A | * 8/1976 | McClean | 264/102 |
| 4,229,838 A | 10/1980 | Mano | |
| RE30,658 E | 6/1981 | Arvidsson | |
| 4,286,341 A | 9/1981 | Greer et al. | |
| 4,304,010 A | 12/1981 | Mano | |
| 4,784,659 A | 11/1988 | Fleckenstein et al. | |
| 4,806,595 A | 2/1989 | Noishiki et al. | |
| 4,822,361 A | 4/1989 | Okita et al. | |
| 4,842,575 A | 6/1989 | Hoffman, Jr. et al. | |
| 4,857,124 A | * 8/1989 | Shobert et al. | 156/149 |
| 4,883,550 A | 11/1989 | Overath et al. | |
| 4,902,290 A | 2/1990 | Fleckenstein et al. | |
| 4,911,713 A | 3/1990 | Sauvage et al. | |
| 4,931,306 A | 6/1990 | Pinkhasov | |
| 5,108,424 A | 4/1992 | Hoffman, Jr. | |
| 5,181,903 A | 1/1993 | Vann et al. | |
| 5,197,977 A | 3/1993 | Hoffman, Jr. et al. | |
| 5,298,276 A | 3/1994 | Jayarman | |
| 5,340,614 A | 8/1994 | Perman et al. | |
| 5,376,118 A | * 12/1994 | Kaplan et al. | 623/23.72 |
| 5,407,616 A | * 4/1995 | Dube | 264/40.1 |
| 5,410,016 A | 4/1995 | Hubbell et al. | |
| 5,508,060 A | 4/1996 | Perman et al. | |
| 5,529,914 A | 6/1996 | Hubbell et al. | |
| 5,628,786 A | * 5/1997 | Banas et al. | 623/1.13 |
| 5,665,114 A | 9/1997 | Weadock et al. | |
| 5,810,860 A | * 9/1998 | Adrian | 606/169 |
| 5,854,382 A | 12/1998 | Loomis | |
| 6,316,522 B1 | * 11/2001 | Loomis et al. | 523/105 |

OTHER PUBLICATIONS

Sawhney, A.S., Pathak, D.P. and J.A. Hubbell, *Macromolecules*, vol. 26, p. 581–587 (1993).

* cited by examiner

*Primary Examiner*—Shrive P. Beck
*Assistant Examiner*—Jennifer Kolb Michener
(74) *Attorney, Agent, or Firm*—Hoffmann & Baron, LLP (57) ABSTRACT

A process for impregnating a porous material with a cross-linkable composition is disclosed. The degree of impregnation and placement of the cross-linkable composition within the pores of the porous material can be controlled very precisely through the use of a pressure differential. The pressure differential is effected through a nonreactive gas, a vacuum, or a combination thereof. Medical devices produced using such a method are also disclosed.

17 Claims, 4 Drawing Sheets

PROCESS FOR IMPREGNATING A POROUS MATERIAL WITH A CROSS-LINKABLE COMPOSITION

This application is a continuation of application Ser. No. 09/433,625, filed on Nov. 3, 1999 now U.S. Pat. No. 6,521,284.

FIELD OF THE INVENTION

The present invention relates generally to a method for impregnating a porous material with a cross-linkable composition, as well as a material produced by such a method. After crosslinking, the cross-linkable composition may form a hydrogel upon exposure to a humid environment. More particularly, the present invention relates to utilizing a pressure differential to control the degree of impregnation and the placement of the composition within the porous material.

BACKGROUND OF RELATED TECHNOLOGY

It is generally known to provide an implantable material, such as a prosthetic device, with a composition which is either coated onto, or impregnated within, the material in order to render the material impermeable to fluid. In certain applications, bioresorbable compositions are provided for this purpose. In such cases, the composition is resorbed over time and tissue ingrowth encapsulates the prosthesis. Therapeutic agents may additionally be incorporated into the composition, or added subsequently. If the material has low surface activity, application of the composition may require pretreatment of the material.

Various methods of providing compositions which may be coated onto or impregnated into implantable materials are known. It is known to coat textile grafts with a composition by contacting a graft with a composition and subsequently applying pressure, thereby impregnating the graft with the composition. For example, U.S. Pat. Nos. 5,197,977, 4,842,575, and 5,108,424 disclose the use of force to impregnate a textile graft with collagen.

U.S. Pat. No. 4,911,713, to Sauvage et al., describes a process for impregnating knit and woven textile grafts with a solution, thereby rendering the grafts fluid impermeable. The process includes the step of pretreating a graft with a crosslinking agent that reacts with a protein, resulting in a gelatin formation that will render the graft fluid-impermeable. This process allegedly fills the interstices of the textile graft with a solution by controlling gelation time.

U.S. Pat. No. 5,665,114 to Weadock discloses a method of impregnating the pores of implantable prostheses with insoluble, biocompatible, biodegradable materials of natural origin through the use of force. The disclosed method involves clamping one end of a prosthetic, filling the inner lumen of the prosthetic with a composition, and using pressure to cause migration of the composition into the interstices of the ePTFE walls.

Some compositions are so rapidly resorbed as to be of limited usefulness. Crosslinking of polymeric compositions increases their integrity and reduces their rate of resorption. For example, U.S. Pat. Nos. 5,410,016 and 5,529,914 to Hubbell et al. disclose water-soluble coating compositions which form hydrogels when crosslinked (See also, Sawhney, A. S., Pathak, D. P., Hubbell, J. A., *Macromolecules* 1993, 26, 581–587). Additionally, U.S. Pat. No. 5,854,382 discloses water-insoluble polymer systems for impregnation and coating which are cross-linkable to form hydrogels.

Various applications require the use of porous materials, particularly prosthetic devices, to have very specific characteristics relating to the rate of bioresorption of compositions associated with the material, the degree of fluid impermeability of the material, and the ability of the material to promote endothelial cell adhesion and proliferation and smooth muscle cell ingrowth. For example, when a porous material is less than one hundred percent impregnated with a cross-linkable composition, tissue ingrowth, such as smooth muscle cell ingrowth, is promoted. These specific characteristics will determine the suitability of a particular prosthetic device for a particular medical application.

A disadvantage of known techniques of coating and impregnating porous implantable materials is the inability to control the degree, uniformity, and placement of an impregnating composition within the pores of a porous material. Accordingly, there exists a need for a process which allows a porous material, particularly an implantable prosthetic suitable for use as a medical device, to be impregnated with a composition through the application of pressure, wherein the degree of impregnation of the material, as well as the placement of the composition within specific regions of the material, can be controlled with great precision. There further exists a need for a process which allows the composition to be crosslinked following impregnation in order to secure the composition within the pores of the porous material.

SUMMARY OF THE INVENTION

The present invention relates to a process for controllably impregnating a cross-linkable composition into the pores of a porous material, such as an expanded polytetrafluoroethylene (ePTFE) material through the use of a nonreactive gas, a vacuum, or a combination thereof. The application of gas, vacuum, or a combination of gas and vacuum allows for precise control over the degree of impregnation of the cross-linkable compositions within the pores of the material as well as precise control over the placement of the cross-linkable composition within desired regions of the porous material. The cross-linkable composition is subsequently crosslinked in situ, securing the composition within the pores of the material. The cross-linkable composition may form a hydrogel in a humid environment. The invention also relates to an impregnated implantable member produced by such a process.

In one aspect of the invention, there is provided a process which includes: a) providing a porous material having a wall defined by an inner and an outer surface; b) disposing a cross-linkable composition adjacent to, or in contact with, one of the inner or outer surfaces; c) effecting a pressure differential across the inner and outer surfaces through a pressure means selected from the group consisting of a nonreactive gas, a vacuum, or a combination thereof, wherein the pressure on the surface adjacent to or in contact with the cross-linkable composition is greater than the pressure on the surface not in contact with the cross-linkable composition, the pressure differential causing the cross-linkable composition to controllably impregnated the porous material; and d) effecting crosslinking of the cross-linkable composition within the porous material.

The process includes spacing the porous material concentrically about a mandrel to define a cavity therebetween to receive the cross-linkable composition, the mandrel comprising one or more openings for communicating the non-reactive gas, the vacuum, or the combination thereof. The process further includes the step of conducting the controlled impregnation in a pressure chamber.

In a further aspect of the invention, there is provided a process which includes: a) providing a porous material with a wall defined by an inner and an outer surface; b) disposing a cross-linkable first composition adjacent to, or in contact with, one of the inner or the outer surfaces; c) disposing a second composition adjacent to, or in contact with, the other of the inner or the outer surfaces not in contact with, or adjacent to, the first cross-linkable composition; d) effecting a first pressure differential across the wall of the porous material to cause one of the cross-linkable first composition and the second composition to impregnate the porous material by means of a nonreactive gas, a vacuum, or a combination thereof; e) effecting a second pressure differential across the wall of the porous material to cause the other of the cross-linkable first composition and the second composition to impregnate the porous material by means of a nonreactive gas, a vacuum, or a combination thereof; f) effecting crosslinking of the cross-linkable first composition within the porous material.

The process includes spacing the porous material concentrically about a mandrel, the mandrel comprising one or more openings for receiving the nonreactive gas, the vacuum, or the combination thereof, wherein the porous material and the mandrel define a cavity into which the cross-linkable composition may placed, and wherein the controlled impregnation is conducted in a pressure chamber.

The present invention further relates to impregnated implantable materials, such as medical devices. An impregnated implantable material of the present invention includes a porous material produced by the process including: a) providing a porous material having a wall defined by an inner and an outer surface; b) disposing a cross-linkable composition adjacent to, or in contact with, one of the inner or the outer surfaces; c) effecting a pressure differential across the inner and outer surfaces through a pressure means selected from the group consisting of a nonreactive gas, a vacuum, or a combination thereof, wherein the pressure on the surface adjacent to or in contact with the cross-linkable composition is greater than the pressure on the surface not in contact with the cross-linkable composition, the pressure differential causing the cross-linkable composition to controllably impregnated the porous material; and d) effecting crosslinking of the cross-linkable composition within the porous material.

In this process of producing the impregnated implantable member, the porous material is spaced concentrically about a mandrel, the mandrel comprising one or more openings for receiving the nonreactive gas, the vacuum, or the combination thereof, wherein the porous material and the mandrel define a cavity into which the cross-linkable composition may be placed.

The cross-linkable composition may be flowable and may be selected from the group consisting of polymers and copolymers. The composition may be a neat liquid, an emulsion, a liquid polymer or copolymer, or a polymer or copolymer in a solid phase. Desirably, the cross-linkable composition includes a copolymer which includes a bioresorbable region, a hydrophilic region, and a plurality of cross-linkable functional groups per polymer chain. Further, the copolymer may be a di-block copolymer, a tri-block copolymer, or a star copolymer.

The cross-linkable composition may be crosslinked by high energy radiation, thermal radiation, or visible light, or combinations thereof. Additionally, the composition may include a free radical initiator such as an azo compound or peroxide.

Additionally, the cross-linkable composition may include one or more bio-therapeutic agents such as thrombo-resistant agents, antibiotic agents, anti-tumor agents, cell cycle regulating agents, their homologs, derivatives, fragments, pharmaceutical salts, and combinations thereof.

The cross-linkable composition may also include one or more populations of cells, which may be transfected with a genetic construct. The cells may be able to produce and release a therapeutically useful composition.

DETAILED DESCRIPTION OF THE INVENTION

As illustrated in FIGS. 1–7, the present invention relates to processes by which a cross-linkable composition 14 can be impregnated into the pores of a porous material 6 on the inner surface 22 of the porous material 6, on the outer surface 24 of the porous material 6, or on both the inner surface 22 and outer surface 24 of the porous material 6. In one aspect of the present invention, a cross-linkable composition 14 is introduced to the inner surface 22 of porous material 6 and is impregnated into the pores thereof. Such impregnation can be accomplished by several methods, including, but not limited to, the use of a nonreactive gas to effectuate a positive pressure, the use of a vacuum to effectuate a negative pressure, and a combination thereof. Several factors will determine the degree of impregnation. These factors include the viscosity of the cross-linkable composition 14, the size of the pores of the porous material 6, the positive and negative pressures being applied as well as the combination of pressure sources used, and the length of time for which the pressures are applied. Consideration of these factors in practicing the present invention allows for precise control over the degree of impregnation as well as the placement of the cross-linkable composition 14 in specific desired regions of the porous material 6.

Figure 1:
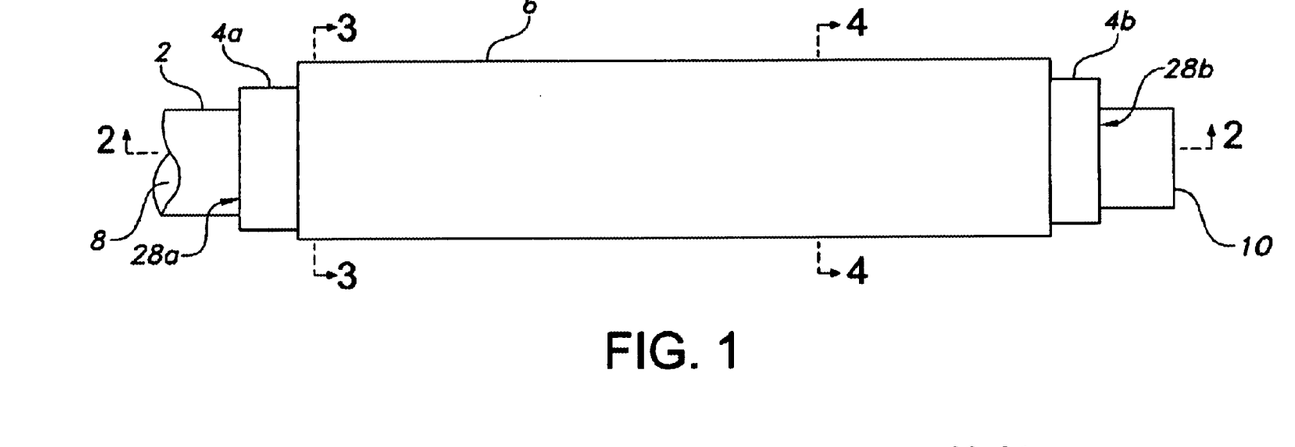
FIG. 1 is a side elevation view of a mandrel, spacers, and a porous material used in the present invention.
Figure 2:
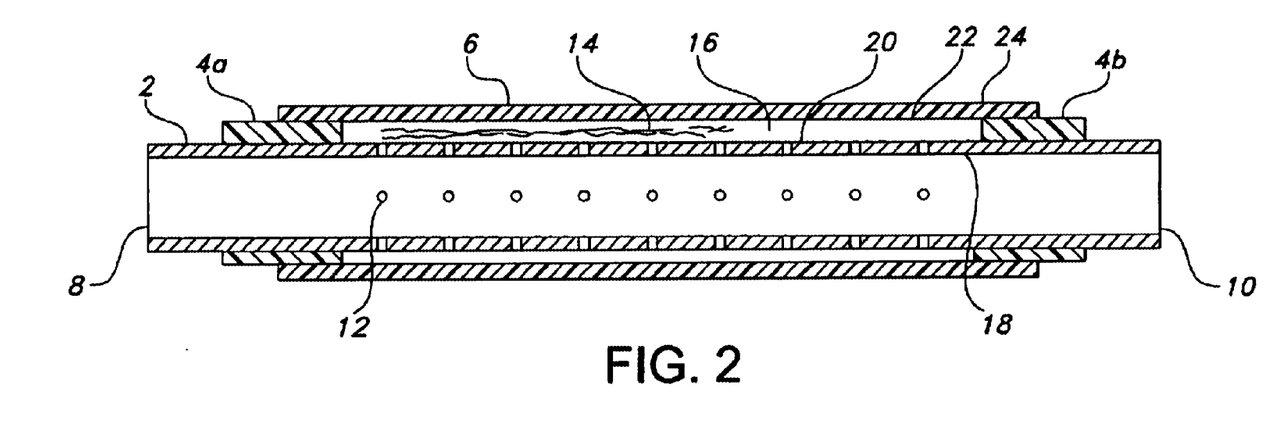
FIG. 2 is a cross-sectional view along line 2—2 of FIG. 1 of a mandrel, spacers, and a porous material used in the present invention.
Figure 3:
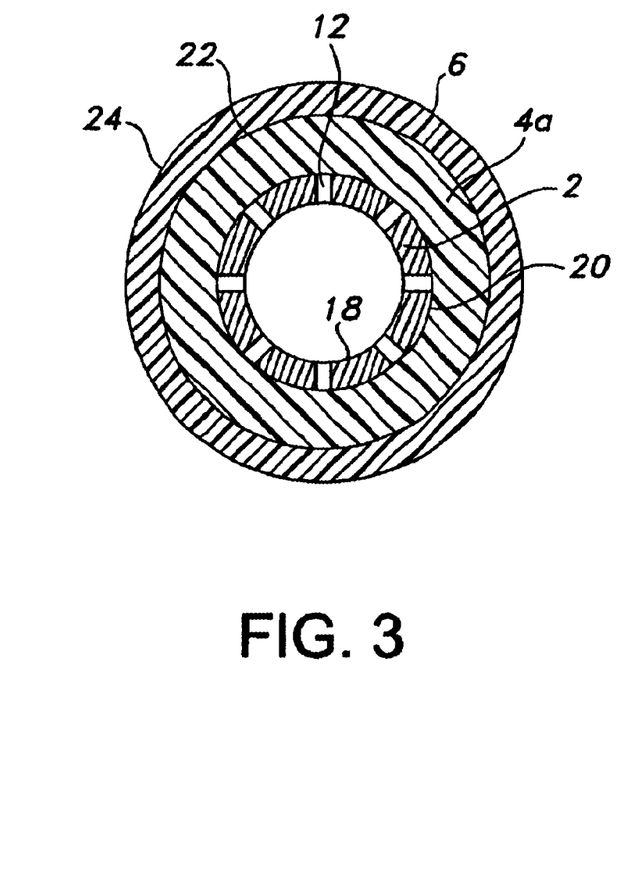
FIG. 3 is a transverse cross-sectional view along line 3—3 of FIG. 1 of a mandrel, a spacer, and a porous material used in the present invention.
Figure 4:
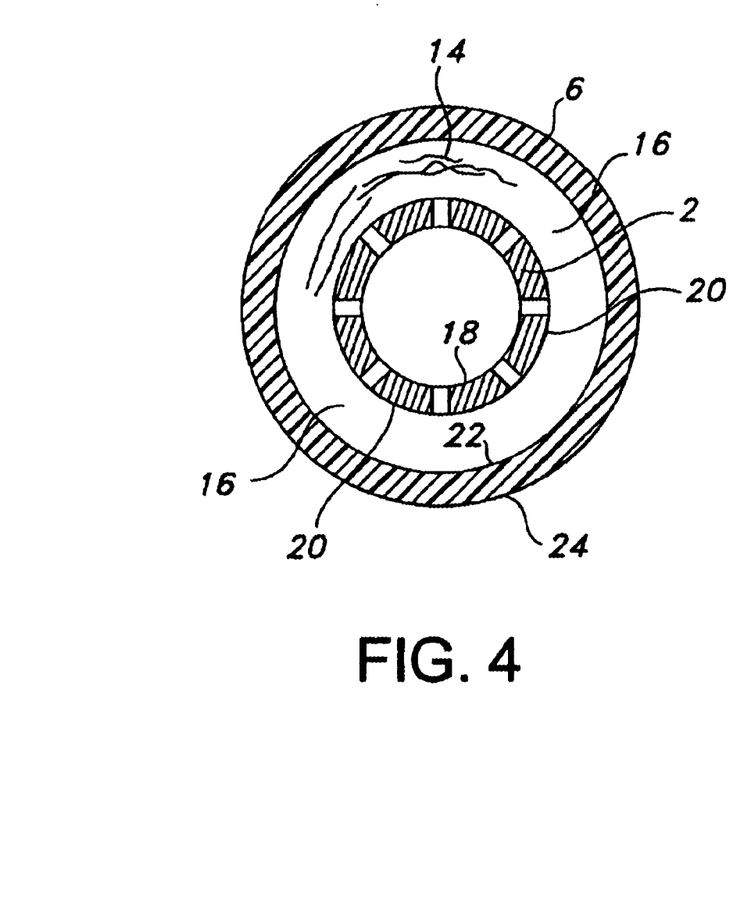
FIG. 4 is a transverse cross-sectional view along line 4—4 of FIG. 1 of a mandrel and a porous material used in the present invention.

In one aspect of the invention, a porous material 6 is coaxially aligned with and spaced concentrically about the outer surface 20 of a mandrel 2 through the use of spacers 4a and 4b, as illustrated in FIGS. 1–4. Mandrel 2 is hollow, is open on end 8, and is closed on end 10. End 8 and end 10 define a passageway with fluid communication therebetween. Mandrel 2 desirably includes openings 12 which permit passage of fluids therethrough. As seen in FIGS. 2 and 4, a cavity 16 for receiving a cross-linkable polymer composition is defined by spacers 4a and 4b, mandrel 2, and porous material 6.

In one aspect of the invention, cross-linkable composition 14 is disposed within cavity 16 such that cross-linkable composition 14 is either adjacent to, but not in contact with, or in contact with, inner surface 22 of porous material 6. A pressure is applied to the cross-linkable composition 14 by disposing a nonreactive gas within the lumen of mandrel 2 through open end 8 thereof. Gases which may be used desirably include inert gases, but may include any gases that do not interfere with the crosslinking reaction and that do not cause the cross-linkable composition 14 to crosslink as it is being impregnated into porous material 6. The particular mandrel 2 used may be any device that is suitable for use in the process of the present invention. The mandrel 2 may be made of any suitable material, such as sintered metal, ceramic, polymeric materials, and glass. Desirably, the mandrel 2 may have openings 12 which are micropores that permit passage of gases but do not permit passage of other materials, such as the cross-linkable composition 14 used in the present invention. The mandrel 2 may have pores that are of any size which are suitable for purposes of the present invention and may be apertured in a known manner.

As seen in FIGS. 2–4, spacers 4a and 4b may be used to maintain porous material 6 above the outer surface 20 of the mandrel 2, while not permitting contact therewith. Any device which prevents the porous material 6 from contacting the mandrel 2 may be suitable for use as spacers 4a and 4b. Spacers 4a and 4b will desirably be used where the openings 12 of the mandrel 2 are small enough to allow gas to pass through but not to allow cross-linkable composition 14 to pass through. The spacers 4a and 4b may be, for example, an end cap that is made of potting compound. If the porous material 6 is placed directly on the outer surface 20 of the mandrel 2, spacers 4a and 4b are not used and the cross-linkable composition 14 is placed in the lumen of the mandrel 2. In such a case, the openings 12 of the mandrel 2 must be of a sufficient size to allow the cross-linkable composition 14 to pass through. The porous material 6 is desirably formed as a tubular structure, as in FIGS. 1 and 2, but may also be formed as other structures, such as sheets. It is contemplated that porous materials in many forms may be impregnated through the process of the present invention.

When cross-linkable composition 14 is disposed within cavity 16 and pressurized gas is provided to the lumen of mandrel 2, the gas will pass through openings 12 of mandrel 2 and contact cross-linkable composition 14. This results in a pressure differential across the inner surface 22 and outer surface 24 of porous material 6. For the purpose of the present invention, a pressure differential is the difference between a first pressure $P_1$ on a first surface and a second pressure $P_2$ on a second surface, where $P_1$ is greater than $P_2$. In the present invention, a pressure differential is effectuated by the application of a nonreactive gas, such as an inert gas, a vacuum, or a combination of a nonreactive gas and a vacuum to a surface of a porous material 6 being impregnated. In this aspect of the invention, the pressure differential is such that the pressure at the inner surface 22 is greater than the ambient atmospheric pressure at the outer surface 24. This pressure differential results in cross-linkable composition 14 impregnating the pores of porous material 6.

For purposes of the present invention, it is contemplated that pressure differentials ranging from 0.1 pounds per square inch (psi) to 10.0 psi are suitable. Desirably, the pressure differential is between 2 psi and 5 psi. These ranges are exemplary only, and are not meant in any way to limit the pressure differential which can be used in the present invention.

Once the cross-linkable composition 14 has impregnated the porous material 6 to the desired degree and in the desired regions, excess cross-linkable composition 14 may be removed and the remaining cross-linkable composition 14 is crosslinked, thereby securing it to the porous material 6. Crosslinking cross-linkable composition 14 prevents water-soluble compositions, or water-soluble components of compositions, from being washed out of porous material 6 when exposed to an aqueous environment. Crosslinking additionally prevents the cross-linkable composition 14 from bioresorbing to an undesired degree or at an undesired rate when placed in situ. As a result, porous prosthetic devices can be made by the process of the present invention which have very specific bioresorption and fluid permeability characteristics. The cross-linkable composition 14 may be crosslinked by means of high energy radiation including, but not limited to, ultraviolet radiation, electron beam or gamma radiation, low energy radiation, such as microwave radiation, thermal radiation, visible light, and combinations thereof. Alternatively, crosslinking may be affected by free radical initiators, such as azo compounds or peroxides. Particularly, the crosslinking agent may be 2,2'-Azobis (N,N'dimethyleneisobutyramidine) dihydrochloride or benzoyl peroxide. The degree of crosslinking may be varied to control the degree and rate of bioresorption of the crosslinked composition.

Desirably, the cross-linkable composition 14 will form a hydrogel when introduced into a humid environment, either prior to, or subsequent to, crosslinking. For purposes of the present invention, a humid environment is one containing about 20% to about 100% water, desirably about 60% to about 100% water. The water may be in either a liquid or a gaseous phase. Hydrogels which may be used in the present invention are polymeric materials that swell in water without dissolving and that retain a significant amount of water. Such materials are characterized by properties that are intermediate between those of liquids and solids. Hydrogels also deform elastically and then recover to their original form, yet will often flow at high levels of stress. Thus, for purposes of the present invention, hydrogels are swollen, three-dimensional networks of hydrophilic polymers. The amount of swelling of the hydrogel can be controlled by controlling the degree of crosslinking that occurs.

Figure 5:
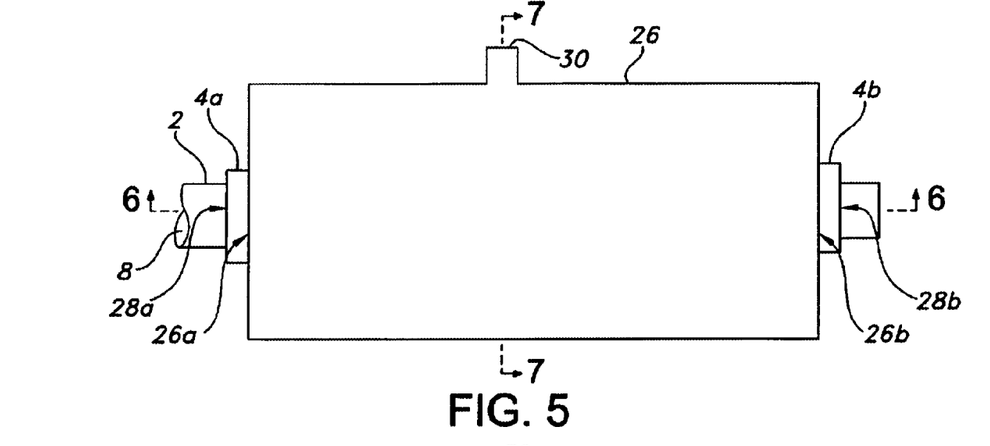
FIG. 5 is a side elevation view of a mandrel, spacers, and a chamber used in the present invention.
Figure 6:
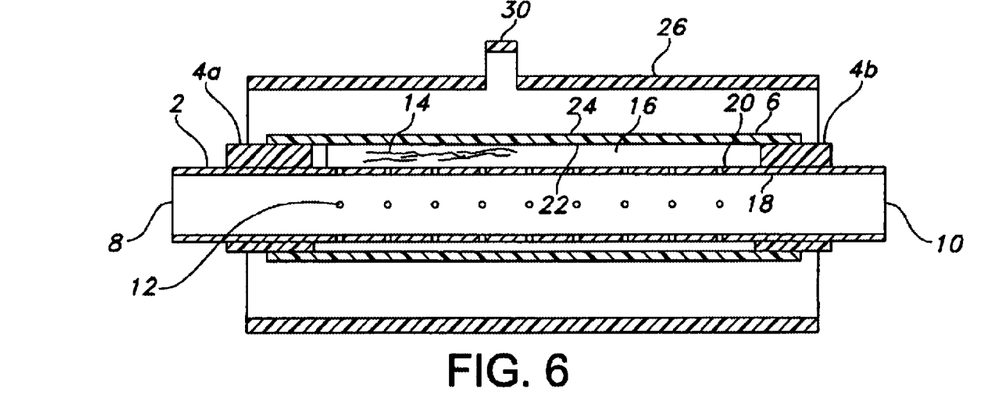
FIG. 6 is a cross-sectional view along line 6—6 of FIG. 5 of a mandrel, spacers, porous material, and a chamber used in the present invention.
Figure 7:
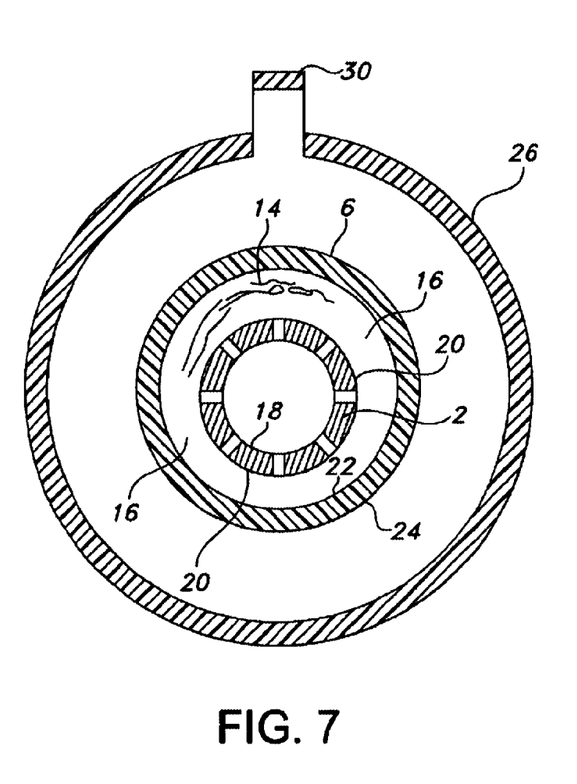
FIG. 7 is a transverse cross-sectional view along line 7—7 of FIG. 5 of a mandrel, porous material, and a chamber used in the present invention.

In another aspect of the present invention, a vacuum is used to effectuate a pressure differential in order to cause a cross-linkable composition 14 to impregnate the pores of porous material 6 at inner surface 22. The porous material 6, mandrel 2, spacers 4a and 4b, and cross-linkable composition 14 are arranged as above. This arrangement is placed within substantially elongate cylindrically-shaped chamber 26, as illustrated in FIGS. 5–7. As set forth above, spacers 4a and 4b and mandrel 2 are arranged such that fluid-tight and gas-tight seals exist at central apertures 26a and 26b of chamber 26, and at central apertures 28a and 28b on spacers 4a and 4b, respectively. Additionally, open end 8 of mandrel 2 is sealed off. As a result, fluid entry into the system is only permitted at opening 30 of chamber 26.

Chamber 26 may be any device that is suitable for use in the present invention. It may be of any design and may be made of any material that allows it to function in the present invention. Such materials include, but are not limited to, sintered metal, ceramic, polymeric materials, and glass. Chamber 26 maintains an internal pressure which is independent of the atmospheric pressure.

A source for effectuating a vacuum, such as a vacuum pump, is attached to opening 30 and a vacuum is drawn. This results in a pressure differential across the inner surface 22 and outer surface 24 of porous material 6, such that the pressure at outer surface 24 is less than the pressure at inner surface 22. As a result of this pressure differential, cross-linkable composition 14 is drawn into the pores of porous material 6 at inner surface 22 thereof. The cross-linkable composition 14 is then crosslinked and may form a hydrogel, as set forth above.

In another aspect of the invention, porous material 6, mandrel 2, spacers 4a and 4b, and cross-linkable composition 14 are arranged within substantially elongate cylindrically-shaped chamber 26, as set forth above. A combination of a vacuum and a nonreactive gas is applied to the arrangement in the manners set forth above. This combination allows for precise control over the degree of impregnation of cross-linkable composition 14 into the pores of porous material 6 and the placement of cross-linkable composition 14 within the pores of porous material 6. Once the cross-linkable composition 14 has impregnated the pores of porous material 6, it is then crosslinked and may form a hydrogel, as set forth above.

In a further aspect of the present invention, a cross-linkable composition 14 is introduced to the outer surface 24 of porous material 6 and is impregnated into the pores thereof. Such impregnation can be accomplished by several methods, including, but not limited to, the use of a nonreactive gas to effectuate a positive pressure, the use of a vacuum to effectuate a negative pressure, and a combination thereof. By selecting the length of time of pressure application, the pressures to be applied, and the combination of methods for effectuating the pressure differential, the rate and degree of impregnation of porous material 6 by the cross-linkable composition 14 can be controlled very precisely. Through these methods, the placement of the cross-linkable composition 14 in specific desired regions of the porous material 6 can be controlled very precisely as well.

In one aspect of the invention, a mandrel 2, porous material 6, and spacers 4a and 4b are arranged as set forth in FIGS. 1–4. Alternatively, porous material 6 may be in contact with the outer surface 20 of mandrel 2, obviating the need for spacers 4a and 4b. A cross-linkable composition is disposed on the outer surface 24 of porous material 6, as seen in FIGS. 2 and 4. A vacuum is applied to the system by attaching a vacuum source to open end 8 of mandrel 2, thereby creating a pressure differential across the inner surface 22 and outer surface 24 of porous material 6, such that the pressure at inner surface 22 is less than the pressure at outer surface 24. As a result, cross-linkable composition 14 is drawn into the pores of porous material 6 at outer surface 24, thereof. The cross-linkable composition 14 is then crosslinked and may form a hydrogel, as set forth above.

In another aspect of the present invention, porous material 6, mandrel 2, spacers 4a and 4b, and cross-linkable composition 14 are arranged within substantially elongate cylindrically-shaped chamber 26, as seen in FIGS. 5–7. Porous material 6 may be in contact with the outer surface 20 of mandrel 2, obviating the need for spacers 4a and 4b. Open end 8 of mandrel 2 is sealed off and a nonreactive gas is applied to the system through opening 30 of substantially elongate cylindrically-shaped chamber 26, creating a pressure differential across the surfaces of porous material 6 such that the pressure at the outer surface 24 is greater than the pressure at the inner surface 22. As a result, cross-linkable composition 14 is forced into the pores of porous material 6 at the outer surface 24 thereof. The cross-linkable composition 14 is then crosslinked and may form a hydrogel, as set forth above.

In another aspect of the invention, porous material 6, mandrel 2, spacers 4a and 4b, and cross-linkable composition 14 are arranged as above within substantially elongate cylindrically-shaped chamber 26, as seen in FIGS. 6 and 7. Porous material 6 may be in contact with the outer surface 20 of mandrel 2, obviating the need for spacers 4a and 4b. A combination of a vacuum and a nonreactive gas is applied to the arrangement in the manners set forth above. This combination allows for precise control over the degree of impregnation of cross-linkable composition 14 into the pores of porous material 6 and over the placement of cross-linkable composition 14 within the pores of porous material 6. Once the cross-linkable composition 14 has impregnated the pores of porous material 6, it is then crosslinked and may form a hydrogel, as set forth above.

In a further aspect of the invention, both inner surface 22 and outer surface 24 of porous material 6 may have cross-linkable composition 14 and an additional composition disposed thereon, respectively. Porous material 6, mandrel 2, and spacers 4a and 4b, are arranged within substantially elongate cylindrically-shaped chamber 26, as seen in FIGS. 5–7. Cross-linkable composition 14 and the additional composition can be the same or different. Porous material 6 may be in contact with the outer surface 20 of mandrel 2, obviating the need for spacers 4a and 4b. In successive steps, a combination of nonreactive gases, a combination of vacuums, or a nonreactive gas and vacuum combination, can be applied to the above arrangement at opening 30 of chamber 26 and/or at open end 8 of mandrel 2. In this aspect, successive pressure differentials are effectuated across inner surface 22 and outer surface 24 of porous material 6, causing cross-linkable composition 14 and the additional composition to impregnate inner surface 22 and outer surface 24, respectively. By controlling the pressures and the length of application of the gases and/or vacuums, the rate and degree of impregnation of both compositions can be controlled, as can the placement of the cross-linkable composition 14 and the additional composition within the pores of porous material 6. Once cross-linkable composition 14 and the additional compound have impregnated the pores of porous material 6, one or both are crosslinked and may form a hydrogel, as set forth above. Alternatively, cross-linkable composition 14 and the additional composition can be such that they will react with each other, thereby causing one or both of cross-linkable composition 14 and the additional composition to crosslink.

The method of the present invention can be used with simple structures, such as basic tubular structures, or with complex structures, such as complex tubular structures. For example, branched tubular structures may be used in the present invention. Such structures would have desired fluid impermeability characteristics when subjected to the process of the present invention. Additionally, the process of the present invention may be used to form thick regions in an implantable material, thereby decreasing radial expansion in the material. Further, elastic polymer compositions could be added to a material used in the present invention to increase the resiliency of the material. Cross-linkable compositions could also be used as anchors for fastening delicate tubular structures.

Porous materials which may be used in the present invention can include, for example, polymeric compositions, non-polymeric compositions, and combinations thereof. The polymeric materials can include, for example, olefin polymers, including polyethylene, polypropylene, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), polyurethane, polyurea, silicone rubbers, polyamides, polycarbonates, polyaldehydes, natural rubbers, polyester copolymers, styrene-butadiene copolymers, polyethers, such as fully or partially halogenated polyethers, and combinations thereof. Non-polymeric implantable materials can include, for example, ceramics, metals, inorganic glasses, pyrolytic carbon and combinations thereof. The implantable materials set forth above are intended to be exemplary only and should not be construed to limit in any way the types of materials which may be used in the present invention.

The implantable materials used in the present invention may be used to manufacture medical devices, such as for example, endoprostheses. Grafts, stents and combination graft-stent devices are contemplated, without limitation. Desirably, these medical devices are vascular or endovascular grafts. Useful vascular or endovascular grafts include those which are knitted, braided or woven textiles, and may have velour or double velour surfaces. These medical devices are desirably manufactured from an extruded polymer, such as polytetrafluoroethylene, particularly expanded polytetrafluoroethylene, polyethylene terephthalate, fluorinated ethylene propylene copolymer (FEP), polyurethane, silicone and the like. Composite structures are also contemplated.

Any cross-linkable composition can be used in the process of the present invention provided that the cross-linkable composition serves to render the porous material into which it is being impregnated impermeable to fluid to a desired degree. Desirably, for the purposes of the present invention, the cross-linkable composition is a bioresorbable polymeric composition and is easily hydrolyzed in the body, or broken down through enzymatic activity.

Accordingly, a cross-linkable composition used in the method of the present invention desirably comprises a polymer or copolymer composition, which may comprise, poly(ethylene glycol). The hydrolytically labile extensions may be a poly($\alpha$-hydroxy acid), such as polyglycolic acid or polylactic acid. See, Sawhney, A. S., Pathak, C. P., Hubbell, J. A., *Macromolecules* 1993, 26, 581–587.

The cross-linkable polymer systems described by Hubbell comprise a biodegradable, polymerizable macromonomer having a solubility of at least about 1 g/100 ml in an aqueous solution. The macromonomer described in Hubbell comprises at least one water-soluble region, at least one degradable region which is hydrolyzable in vivo, and free radical polymerizable end groups having the capacity to form additional covalent bonds to cause macromonomer interlinking, wherein the polymerizable end groups are separated from each other by at least one degradable region.

Cross-linkable compositions useful in the present invention may be a covalently cross-linkable composition which may be applied to a medical device. The composition may include a hydrogel which is formed by crosslinking a substantially water-insoluble copolymer comprised of a bioresorbable region, a hydrophilic region, and a plurality of cross-linkable functional groups per polymer chain.

Additionally, compositions useful in the present invention include multi-block copolymers including, for example, di-block copolymers, tri-block copolymers, star copolymers, and the like. A typical tri-block copolymer may have the following general formula:

xABAx   (I)

wherein A is the bioresorbable region, B is the hydrophilic region and x is the cross-linkable functional group.

A specific example of a copolymer useful in the present invention has the following chemical structure:

but is not limited to, a neat liquid, an emulsion, a liquid polymer or copolymer, or a polymer or copolymer in a solid phase. Suitable cross-linkable polymer compositions of the present invention, and the means by which they may be wherein x is from about 10 to about 100 and y is from about 50 to about 500.

A more specific example of a copolymer useful in the present invention has the following chemical structure:

crosslinked, are set forth in U.S. Pat. Nos. 5,410,016 to Hubbell et al., 5,529,914 to Hubbell et al., and 5,854,382 to Loomis, all herein incorporated by reference. The present invention may also include cross-linkable polymer groups such as free isocyanate and urethanes.

Both of the Hubbell patents disclose water-soluble systems which include block copolymers having a water-soluble central block segment sandwiched between two hydrolytically labile extensions. Such copolymers are further end-capped with photopolymerizable acrylate functionalities. These systems form hydrogels when crosslinked. The water-soluble central block of these copolymers may include wherein the ratio of A to B is about 3:1, x is from about 10 to about 100, and y is from about 50 to about 300.

The above polymer compositions are provided for the purpose of illustration only. It is understood that the present invention may involve the use of any cross-linkable composition that is suitable for being associated with a porous material for the purpose of rendering the material impermeable to fluid to a desired degree.

Grafts with self-sealing characteristics can also be made in accordance with the present invention. For example, such grafts can be made by controllably impregnating a porous substrate, i.e., a polymeric or textile implantable material, with cross-linkable compositions which include liquid silicones, polyurethanes, silicone/polyurethane copolymers, (meth)acrylate copolymers, fluoroelastomers, vulcanizable polyolefin oligomers, and the like. Specific examples include, without limitation, polyhydroxyallyl (meth) acrylates, such as polyhydroxyethyl methacrylate, functionalized (meth)acrylates, such as copolymers of lauryl methacrylate and phosphoryl choline, natural rubber, latex emulsions, styrene-butadiene rubber, polyisobutylene, butyl rubber, polyisoprene, polyvinylacetates, and the like. These cross-linkable compositions provide a means for self-sealing after puncture by a percutaneous device, e.g., by a needle or introducer catheter. Products made using these compositions according to the present invention have particular application as vascular grafts, and in particular arterial venous access (AV) grafts. AV access grafts are used in hemodialysis applications. Other grafts, such as endografts, are also contemplated.

In another aspect of the present invention, there is provided a device, such as a medical device, produced by a method of the present invention. Such a medical device may be made from implantable materials and is desirably porous. Examples of such devices are conduits, vascular grafts, endovascular grafts, stents, graft-stents, catheters, guidewires, trocars, introducer sheaths, and surgical patches. Such devices may be made from textile materials, polymeric films, and the like. Devices produced by the method of the present invention will be rendered impermeable to fluid to a desired degree. For purposes of the present invention, impermeability to fluid refers to the specific porosity of a material, such as a porous vascular or endovascular graft. Porosity of materials is often measured with a Wesolowski Porosity tester. With this apparatus, a graft is tied off at one end and the free end is attached to a valve on a porometer so that the graft hangs freely in a vertical position. Then, water is run through the graft for one minute and the water that escapes from the graft is collected and measured. The specific porosity of the graft is then calculated according to the following formula:

$$P = \frac{V}{A}$$

where V is the volume of water collected in ml/min and A is the surface area of the graft exposed to water in $cm^2$. A specific porosity of $\leq 1.0$ $ml/min/cm^2$ is considered an acceptable amount of leakage for an implantable vascular graft. Accordingly, for purposes of this invention, a substantially fluid impermeable material means a material with a specific porosity, after impregnation with a cross-linkable composition used in the method of the present invention, of about $\leq 1.0$ $ml/min/cm^2$.

A medical device of the present invention may also be a catheter, a guidewire, a trocar, an introducer sheath, or the like. When introduced to such devices, cross-linkable compositions used in the present invention impart increased bio-compatibility to the device. Furthermore, when a cross-linkable composition used in the present invention includes a drug or bio-active agent, specific therapeutic effects can be imparted to such devices. Moreover, a hydrophilic region of a cross-linkable composition used in a method of the present invention can impart increased lubriciousness to, for example, a guidewire or other similar device.

Thus, any medical device to which a cross-linkable composition used in the present invention can adhere may be used in the present invention. Accordingly, the examples of implantable materials and medical devices set forth above are for purposes of illustration only and are not intended to limit the scope of the materials and devices which may be used in the present invention.

In another embodiment of the present invention, a cross-linkable composition used in the present invention may be used in tissue engineering applications as supports for one or more populations of cells. These cells may be transfected with a genetic construct and may be capable of releasing a therapeutically useful compositions. Appropriate tissue scaffolding structures are known, such as the prosthetic articular cartilage described in U.S. Pat. No. 5,306,311 (incorporated by reference herein). Methods of seeding and/or culturing cells in tissue scaffoldings are also known. Additionally, cross-linkable compositions used in a method of the present invention may be used to encapsulate cells for tissue engineering purposes.

The cross-linkable compositions used in the present invention may have incorporated therein one or more agents, such as bio-therapeutic agents. These bio-therapeutic agents include pharmaceutical agents which may be incorporated such that they are released as the cross-linkable composition is bioresorbed. Thus, a material produced by a method of the present invention may be used to target therapeutic agents to specific sites of the body. Further, the rate of bioresorption of the cross-linkable compositions used in the present invention may be controlled by selectively choosing a particular ratio of bioresorbable to hydrophilic regions in the cross-linkable compositions. As such, certain cross-linkable compositions which may be used in the present invention are capable of delivering quantities of a therapeutic agent to a specific site in the body as the cross-linkable composition is bioresorbed.

Any drug or bio-therapeutic agent may be incorporated into a cross-linkable composition used in the present invention, provided that it does not interfere with the desired characteristics and functions of the cross-linkable composition as set forth above. Examples of suitable drugs or bio-therapeutic agents may include, without limitation, thrombo-resistant agents, antibiotic agents, anti-tumor agents, cell cycle regulating agents, their homologs, derivatives, fragments, pharmaceutical salts, and combinations thereof.

Useful thrombo-resistant agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics may include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof Useful anti-viral agents may include, for example, amantadines, rimantadines, ribavirins, idoxuridines, vidarabines, trifluridines, acyclovirs, ganciclovirs, zidovudines, foscamets, interferons, their homologs, analogs, fragments, derivatives, pharmaceutical salts and mixtures thereof.

EXAMPLE 1

An 80 cm length of a porous expanded polytetrafluoroethylene vascular graft (Exxcell™, catalog number 391084, 4 mm nominal diameter with 0.45 mm wall thickness; manufactured by the Meadox division of Boston Scientific Corporation, Natick, Mass.) was arranged as in FIGS. 1–4. The space between the mandrel and the luminal surface of the graft was filled with cross-linkable composition A, as seen in FIGS. 2 and 4.

Composition A:

grams of xABAx triblock polymer, where x=acrylate ester end-groups; A=polylactate (15 repeat units); B=poly (ethylene glycol-co-propylene glycol), dihydroxy functional, avg. $M_n$ ca. 12,000, 75% ethylene glycol from Aldrich Chemical Company, catalog number 43820-0.

13.5 milligrams of 2,2'-azobis[2-(2-imidazolin-2-yl) propane] dihydrochloride from Wako Chemical Company, Osaka Japan.

4.0 grams of deionized water.

Procedure:

The porous mandrel was slowly pressurized with argon while the outer surface of the graft was exposed to atmospheric pressure. The pressure differential across the wall of the graft was maintained at between 4.0 psi and 5.0 psi for 15 minutes. Under these controlled conditions, composition A did not exude through the wall of the graft to the outer surface. The graft was removed from the apparatus and excess composition A was wiped from the lumen. The graft was then transferred to a chamber maintained at 70° C., >90% relative humidity, with the exclusion of oxygen (argon atmosphere maintained).

After 60 minutes, the graft was removed from the chamber and washed for 5 minutes with 25 ml of deionized water followed by thorough rinsing in deionized water and drying in vacuo at 50–60° C. The weight of the resulting dehydrated crosslinked composition A fixed into the wall of the graft was 1.21% of the weight of the non-impregnated substrate. This dehydrated crosslinked composition A was clearly visible in a scanning electron micrograph of a cross-section of the graft.

Although illustrative embodiments of the present invention have been described herein, it should be understood that the invention is not limited to those described, and that various other changes or modifications may be made by one skilled in the art without departing from the scope or spirit of the invention.

What is claimed is:

1. A process for controllably impregnating a composition into a porous material comprising the following sequential steps of:
    (a) providing a hollow mandrel having an inner surface, an outer surface, and openings between said inner surface and said outer surface;
    (b) placing a porous material, having a wall defined by an inner surface and an outer surface around said mandrel, wherein said inner surface of said porous material is adjacent to said outer surface of said mandrel;
    (c) disposing a composition into a location related to said mandrel or said porous materials which is selected from one of:
        (i) a location adjacent to or in contact with said inner surface of said porous material; or
        (ii) a location adjacent to or in contact with said outer surface of said porous material; or
        (iii) a location adjacent to or in contact with said inner surface of said mandrel;
    (d) effecting a constant pressure differential between said inner surface and said outer surface of said mandrel by a means selected from the group consisting of:
        (i) a non-reactive gas applied to said inner surface of said mandrel when said composition is in contact with or adjacent to said inner surface of said porous material or said inner surface of said mandrel;
        (ii) a vacuum applied to said outer surface of said porous material when said composition is in contact with or adjacent to said inner surface of said porous material or said inner surface of said mandrel;
        (iii) a combination of a non-reactive gas applied to said inner surface of said mandrel and a vacuum applied to said outer surface of said porous material when said composition is in contact with or adjacent to said inner surface of said porous material or said inner surface of said mandrel;
        (iv) a non-reactive gas applied to said outer surface of said porous material when said composition is adjacent to or in contact with said outer surface of said porous material; and
        (v) a combination of a non-reactive gas applied to said outer surface of said porous material and a vacuum applied to said inner surface of said mandrel when said composition is adjacent to or in contact with said outer surface of said porous material;
    (e) maintaining said constant pressure differential for a period of time sufficient to effect a desired degree of impregnation of said composition into said porous material.

2. The process of claim 1, wherein a pressure on the surface adjacent to or in contact with said composition is greater than a pressure on the surface not in contact with said composition.

3. The process of claim 1, wherein said controllably impregnating is conducted in a pressure chamber.

4. The process of claim 1, wherein said pressure differential is from about 0.1 psi to about 10.0 psi.

5. The process of claim 1, wherein said non-reactive gas is an inert gas.

6. The process of claim 1, wherein said porous material is selected from the group consisting of polymeric materials, non-polymeric materials, and combinations thereof.

7. The process of claim 1, wherein said composition is cross-linkable.

8. The process of claim 7, further comprising the step of effecting crosslinking of said cross-linkable composition within said porous material.

9. The process of claim 8, wherein said cross-linkable composition further comprises on or more bio-therapeutic agents, wherein said bio-therapeutic agents are selected from the group consisting of thrombo-resistant agents, antibiotic agents, anti-tumor agents, cell cycle regulating agents, their homologs, derivatives, fragments, pharmaceutical salts, and combinations thereof.

10. The process of claim 8, wherein said cross-linkable composition is a neat liquid, an emulsion, a liquid polymer or copolymer, or a polymer or copolymer in a solid phase.

11. The process of claim 9, wherein said copolymer is a water-insoluble copolymer comprising a bioresorbable region, a hydrophilic region, and a plurality of cross-linkable functional groups per polymer chain.

12. The process of claim 9, wherein said copolymer has the following chemical structure:

wherein x is from about 10 to about 100 and y is from about 50 to about 500.

13. The process of claim 9, wherein said copolymer has the following chemical structure:

wherein the ratio of A to B is about 3:1, x is from about 10 to about 100, and y is from about 50 to about 300.

14. The process of claim 1, wherein said porous material is a medical device, wherein said medical device is selected from the group consisting of conduits, vascular grafts, endovascular grafts, stents, graft-stents, catheters, guidewires, trocars, and introducer sheaths.

15. The process of claim 1, wherein said composition further comprises one or more populations of cells.

16. The process of claim 1, further comprising the step of removing excess composition from either said inner or said outer surface of said porous material.

17. A process for controllably impregnating a composition into a porous material comprising the sequential steps:

(a) providing a hollow mandrel having an inner surface, an outer surface and openings between said inner surface and said outer surface;

(b) placing a porous material, having a wall defined by an inner surface and an outer surface, wherein said inner and outer surfaces are opposing surfaces, around said mandrel, wherein said inner surface of said porous material is adjacent to said outer surface of said mandrel;

(c) disposing a composition into a location related to said mandrel or said porous materials which is selected from one of:
   (i) a location adjacent to or in contact with said inner surface of said porous material; or
   (ii) a location adjacent to or in contact with said outer surface of said porous material; or
   (iii) a location adjacent to or in contact with said inner surface of said mandrel;

(d) effecting a constant pressure differential between said inner surface and said outer surface of said mandrel by a means selected from the group consisting of:
   (i) a non-reactive gas applied to said inner surface of said mandrel when said composition is in contact with or adjacent to said inner surface of said porous material or said inner surface of said mandrel;
   (ii) a vacuum applied to said outer surface of said porous material when said composition is in contact with or adjacent to said inner surface of said porous material or said inner surface of said mandrel;
   (iii) a combination of a non-reactive gas applied to said inner surface of said mandrel and a vacuum applied to said outer surface of said porous material when said composition is in contact with or adjacent to said inner surface of said porous material or said inner surface of said mandrel;
   (iv) a non-reactive gas applied to said outer surface of said porous material when said composition is adjacent to or in contact with said outer surface of said porous material; and
   (v) a combination of a non-reactive gas applied to said outer surface of said porous material and a vacuum applied to said inner surface of said mandrel when said composition is adjacent to or in contact with said outer surface of said porous material;

(e) maintaining said pressure differential for a period of time sufficient to effect a desired degree of impregnation of said composition into said porous material without causing the composition to pass through the opposing surface of the porous material.

* * * * *

UNITED STATES PATENT AND TRADEMARK OFFICE
CERTIFICATE OF CORRECTION

PATENT NO.    : 6,797,311 B2
DATED         : September 28, 2004
INVENTOR(S)   : G. Loomis et al.

It is certified that error appears in the above-identified patent and that said Letters Patent is hereby corrected as shown below:

Column 2,
Line 56, should read -- ...to controllably impregnate the porous... --.

Column 3,
Lines 40-41, should read -- ...controllably impregnate the porous... --.

Column 12,
Lines 2-3, should read -- a therapeutically useful composition. --.

Signed and Sealed this

Nineteenth Day of April, 2005

JON W. DUDAS
*Director of the United States Patent and Trademark Office*